(12) United States Patent
DeBruin et al.

(10) Patent No.: US 7,863,407 B2
(45) Date of Patent: Jan. 4, 2011

(54) INTEGRATED POLYESTER PRODUCTION FACILITY

(75) Inventors: Bruce Roger DeBruin, Lexington, SC (US); Allan R. Rothwell, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 25 days.

(21) Appl. No.: 12/171,330

(22) Filed: Jul. 11, 2008

(65) Prior Publication Data

US 2009/0039568 A1 Feb. 12, 2009

Related U.S. Application Data

(60) Provisional application No. 60/964,265, filed on Aug. 10, 2007, now abandoned.

(51) Int. Cl.
*C08G 63/02* (2006.01)
*C08G 64/00* (2006.01)

(52) U.S. Cl. .................. 528/272; 422/129; 422/130; 422/131; 422/137; 525/437; 525/439; 526/64; 528/271; 528/308.1

(58) Field of Classification Search ............ 422/129, 422/130, 131, 137; 525/437, 439; 526/64; 528/271, 272, 308.1
See application file for complete search history.

(56) References Cited

U.S. PATENT DOCUMENTS

| | | | |
|---|---|---|---|
| 4,356,142 A | 10/1982 | Germanio | |
| 4,372,910 A | 2/1983 | Stroup et al. | |
| 4,473,515 A | 9/1984 | Ryder | |
| 4,609,721 A | 9/1986 | Kirshenbaum et al. | |
| 5,298,530 A | 3/1994 | Gamble et al. | |
| 5,344,912 A | 9/1994 | Dalgewicz, III et al. | |
| 5,529,195 A | 6/1996 | Valyi | |
| 5,945,460 A | 8/1999 | Ekart et al. | |
| 5,968,429 A | 10/1999 | Treece et al. | |
| 6,099,778 A | 8/2000 | Nelson et al. | |
| 6,472,557 B1 | 10/2002 | Pell, Jr. et al. | |
| 6,848,899 B2 | 2/2005 | Takada et al. | |
| 6,861,494 B2 * | 3/2005 | Debruin | 528/272 |
| 6,986,864 B2 | 1/2006 | Porter | |
| 2002/0137877 A1 | 9/2002 | Debruin | |
| 2004/0230025 A1 * | 11/2004 | DeBruin | 528/271 |
| 2006/0047145 A1 | 3/2006 | Wonders et al. | |

FOREIGN PATENT DOCUMENTS

| | | |
|---|---|---|
| EP | 0839848 A2 | 6/1998 |
| WO | 2006021063 A1 | 3/2006 |

OTHER PUBLICATIONS

Dow in Central Germany 1995-2003, Dow Chemical Company. Retrieved from the Internet <URL www.dow.com/valuepark/news/20013120d_pg2.htm.
What Will New PET Resin Processes Mean to Price, Package Innovation? Aug. 31, 2005. Packaging Strategies. Retrieved from the Internet <URL www.packstrat.com/CDA/Archives/7cd9ea638f2a01VgnVCM100000f932a8c0.
DAK Americas Reports Progress on PET Plant Construction: New plant to use proprietary Melt-Tek a O' manufacturing process; May 11, 2006. DAK Americas. Retrieved from the Internet <URL www.dakamericas. com/newsdetail.asp?ID=52.
Falbe, J. et al., "Rompp Chemie Lexikon," 1992, Georg Thieme Verlag Stuttgart, New York, p. 4504, XP-002499989.

* cited by examiner

*Primary Examiner*—Terressa M Boykin
(74) *Attorney, Agent, or Firm*—Dennis V. Carmen; Steven A. Owen; Bernard J. Graves, Jr.

(57) ABSTRACT

A process for producing terephthalic acid in a TPA facility, polyethylene terephthalate in a PET facility, and containers in a forming facility in which the distance between the TPA facility and the forming facility is less than about 10 miles. There is also described a process for transporting a wet mixture of TPA particles via a convey system to a PET facility. In contrast to traditional processing schemes, the processing steps can be located proximate to each other and can be integrated to eliminate certain intermediate processing steps such as, for example, purification, heating, cooling, and drying.

20 Claims, 1 Drawing Sheet

US 7,863,407 B2

INTEGRATED POLYESTER PRODUCTION FACILITY

RELATED APPLICATIONS

This application claims the priority benefit of U.S. Provisional Pat. App. Ser. No. 60/964,265 filed Aug. 7, 2007, now abandoned, the entire disclosures of which are incorporated herein by reference.

BACKGROUND OF THE INVENTION

1. Field of the Invention

This invention relates to an integrated system for producing melt-phase polyesters and products therefrom. In another aspect, the invention concerns an integrated polyester production facility capable of producing both melt-phase polyesters and products incorporating the melt-phase polyesters.

2. Description of the Prior Art

Polyesters such as polyethylene terephthalate (PET), polyethylene napthalate (PEN), and polybutylene terephthalate (PBT) have widespread utility in a variety of consumer, industrial, and engineering applications. PET is often used in single and multiple use consumer goods such as containers for food and beverage products, cosmetics, pharmaceuticals, and other household items. Advances in process technology coupled with increased demand have lead to an increasingly competitive market for the production and sale of polyesters and polyester products. Therefore, a low-cost, high-efficiency process for producing polyesters and polyester containing products is desirable.

Conventional processing schemes for the production of polyesters and polyester products involve three basic steps: (1) the production of raw materials; (2) the conversion of raw materials into polyester; and (3) the production of polyester containing products. Often, each step is performed in one or more operating facilities located at substantial distances from each other. These substantial distances, which can exceed several hundred miles, greatly increase transportation and logistical costs for both suppliers and customers. In addition, each operating facility must create a final product that can be easily transported and stored for extended periods of time. This need for a stable, transferable product necessitates additional purifying, drying, cooling, and reheating steps in each step of the production process, which adversely impact the capital, operating, and maintenance cost for each facility.

Thus, a need exists for a simple, efficient polyester production facility capable of producing both polyester and polyester products in a way that minimizes overall cost and maximizes production while maintaining a high product quality.

SUMMARY OF THE INVENTION

In one embodiment of the present invention, there is provided a process comprising: (a) producing a terephthalic acid (TPA) product in a TPA facility; (b) using at least a portion of the TPA product to produce a polyethylene terephthalate (PET) product in a PET facility having a design production rate greater than about 4,500 pounds per hour; and (c) using at least a portion the PET product to make containers in a forming facility, wherein the distance between the TPA facility and the forming facility is less than about ten miles.

In another embodiment of the present invention, there is provided a process comprising: (a) producing a wet mixture from a TPA facility, wherein the wet mixture comprises at least about 50 weight percent of solid TPA particles and at least about 1 weight percent of a liquid; (b) transporting the wet mixture from the TPA facility to a PET facility via a convey system; and (c) introducing the wet mixture into the PET facility, wherein the PET facility has a design production rate greater than about 4,500 pounds per hour.

BRIEF DESCRIPTION OF THE DRAWINGS

Certain embodiments of the present invention are described in detail below with reference to the enclosed figure, wherein.

DETAILED DESCRIPTION

Figure 1:
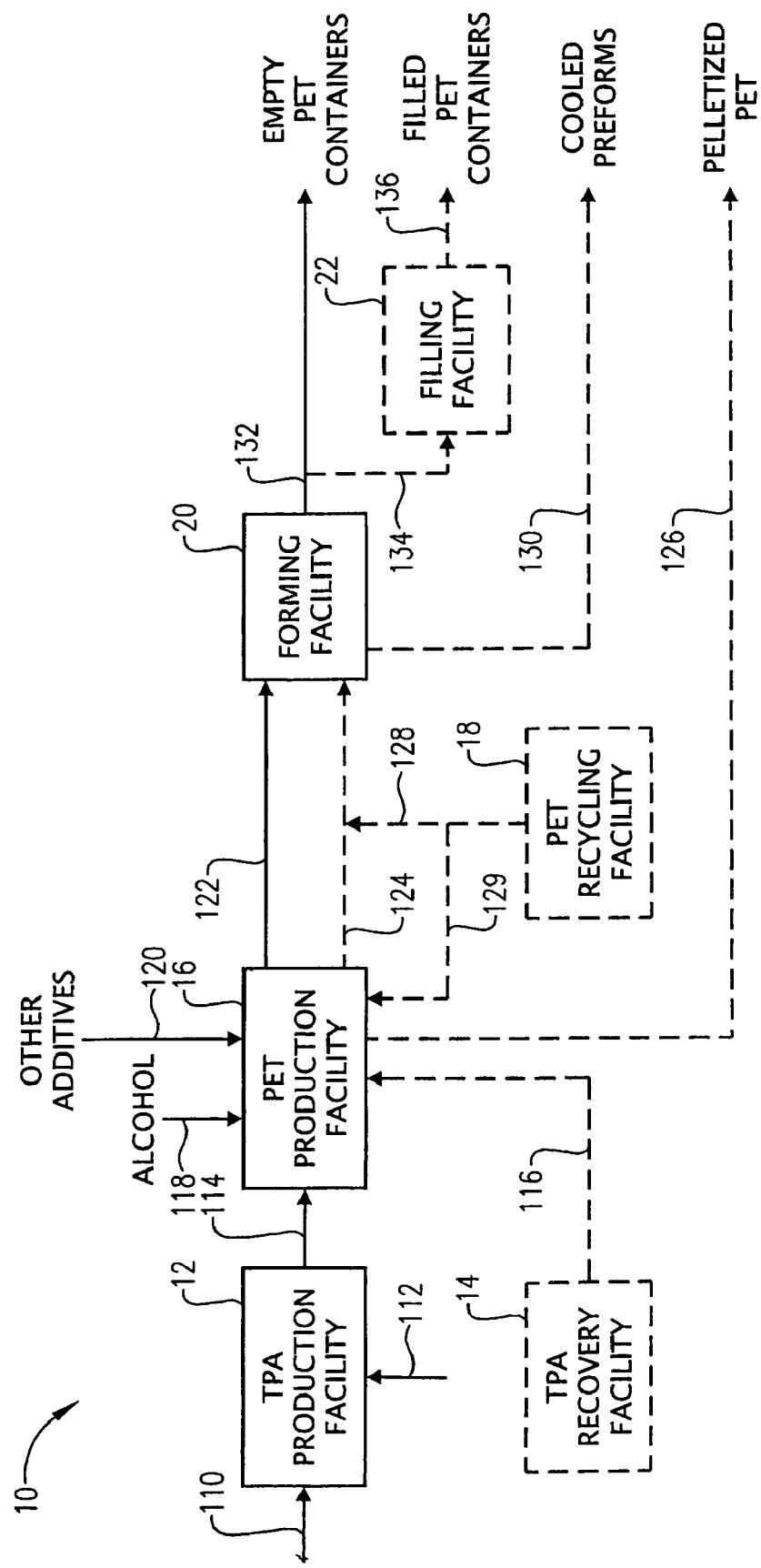
FIG. 1 is a schematic depiction of an integrated polymer production facility in accordance with one embodiment of the present invention.

Referring now to FIG. 1, an integrated polyester production facility 10 according to one embodiment of the present invention is illustrated. Integrated polyester production facility 10 is illustrated as generally comprising a terephthalic acid (TPA) production facility 12, an optional TPA recovery facility 14, a polyethylene terephthalate (PET) production facility 16, an optional PET recycling facility 18, a forming facility 20, and an optional filling facility 22. In general, terephthalic acid or derivatives thereof produced in TPA facility 12 and, optionally, TPA and/or derivatives thereof recovered in TPA recovery facility 14 can be used to produce PET in PET production facility 16. The polyethylene terephthalate exiting PET production facility 16 and/or PET recycling facility 18 can then be molded into beverage containers in forming facility 20 and, optionally, filled with a liquid beverage in filling facility 22 prior to exiting integrated production facility 10 for subsequent transportation and/or sale to customers.

Conventional processing schemes for producing beverage containers from PET involve coordination of numerous remote production facilities, which are often separated by hundreds of miles. In contrast, integrated production facility 10 of the present invention provides a single facility incorporating the production stages in close proximity. For example, in one embodiment of the present invention, the distance between product outlet of TPA production facility 12 and the feed inlet of forming facility 18 can be less than about 10 miles, less than about 5 miles, less than about 2 miles, or less than 1 mile. According to another embodiment, the distance between the product outlet of TPA production facility 12 and/or the product outlet of TPA recovery facility 14 and the feed inlet of PET production facility 16 can be less than about 2 miles, less than about 1 mile, less than about 0.5 miles, or less than 0.25 miles. In a further embodiment, the distance between the product outlet of PET production facility 16 and the feed inlet of forming facility 18 can be less than about 2 miles, less than about 1 mile, less than about 0.5 miles, or less than 0.25 miles.

Integrated polyester production facility 10 can be operated more efficiently than conventional polyester and/or polyester product processing schemes. In one embodiment, integrated production facility 10 can include individual commercial processing facilities having complementary design rates. In general, TPA production facility 10 can have a design TPA production rate of at least about 3,700 pounds per hour (lbs/hr), at least about 5,000 lbs/hr, at least about 50,000 lbs/hr, at least about 100,000 lbs/hr, or at least 200,000 lbs/hr. PET production facility can have a design production rate of at least about 4,500 lbs/hr, at least about 10,000 lbs/hr, at least about 50,000 lbs/hr, at least about 100,000 lbs/hr, or at least 200,000 lbs/hr. Further, the design production rate of TPA production facility 12 can be within about 15 percent, within about 10 percent, within about 5 percent, or within 1 percent of the design TPA feed rate of PET production facility 16.

Turning now to the operation of integrated polyester production facility 10 as illustrated in FIG. 1, a stream in conduit 110 comprising an oxidizable aromatic compound and a solvent enters TPA production facility 12, wherein the aromatic compound is oxidized via the oxygen-containing stream in conduit 112 in the presence of a catalyst or catalyst system. In one embodiment, the oxidizable compound can comprise p-xylene, m-xylene, p-tolualdehyde, m-tolualdehyde, p-toluic acid, m-toluic acid, and/or acetaldehyde. According to one embodiment of the present invention, p-xylene can be oxidized in the presence of a catalyst system comprising cobalt, bromide, and/or manganese and a solvent comprising acetic acid and water. Generally, the oxidation reaction can take place at a temperature in the range of from about 125 to about 200° C., about 150 to about 180° C., or 155 to about 165° C. and a pressure in the range of from about 1 to about 20 bar gauge (barg), about 2 to about 12 barg, or 4 to 8 barg. The oxidation reactor can be any suitable reactor known in the art, including, for example, a bubble column reactor and/or a mechanically agitated reactor.

The reaction products can exit the oxidation reactor (not shown) as a slurry comprising terephthalic acid, terephthalic acid isomers and derivatives, and oxidation byproducts. This "crude" slurry can subsequently be purified in a purification zone (not shown) to remove and/or convert at least a portion of the oxidation byproducts. Suitable purification methods can include, for example, oxidation, hydrogenation, and/or dissolution and recrystallization. The resulting purified slurry can then be sent to a product isolation/catalyst removal zone (not shown), wherein the liquid solvent can be removed from the slurry to thereby produce a wet mixture comprising purified TPA. In one embodiment, the wet mixture can be a wet cake comprising at least about 50 weight percent, at least about 75 weight percent, or at least 85 weight percent solid TPA particles and/or at least about 1 weight percent, at least about 2 weight percent, or at least about 5 weight percent liquid, based on the total weight of the mixture. In one embodiment, the liquid can comprise at least about 25 volume percent, 50 volume percent, or 75 volume percent water. Any centrifuge or filter known in the art for such a separation, including, for example, a pressure drum filter, vacuum drum filter, vacuum belt filter, multiple solid blow centrifuges, and/or a perforated centrifuge can be utilized in TPA production facility 12 to produce the wet TPA mixture.

In contrast to conventional TPA operating facilities that subsequently dry the resulting wet cake to obtain a dried particulate TPA product, TPA production facility 12 can transport wet cake TPA directly to PET production facility 16, which will be discussed in more detail shortly. In general, the temperature of the wet cake TPA transported between the product outlet of TPA production facility 12 and the feed inlet of PET production facility 16 via transportation mechanism 114 can be maintained above about 100° F., above about 150° F., or above 175° F. Transportation mechanism 114 can be any device capable of delivering wet cake TPA to PET production facility over a distance of less than about 2 miles, less than about 1 mile, less than about 0.5 miles, or less than about 0.25 miles. In one embodiment, transportation mechanism 114 can comprise a conveyor or other convey system. In another embodiment, transportation mechanism 114 can comprise a conduit and an associated pneumatic and/or hydraulic driver, such as, for example, a pump.

According to one embodiment of the present invention, at least a portion of the TPA entering PET facility 16 can originate from an optional TPA recovery facility 14. In general, TPA recovery facility 14 can recover terephthalic acid and terephthalic acid derivatives, such as, for example, dimethylterephthalate, from previously used and/or scrap PET by breaking ester bonds to reduce the scrap PET to its monomeric components. Several methods are suitable for use in TPA recovery facility 14 for depolymerizing PET to form recovered TPA. As used herein, the term "recovered terephthalic acid (TPA)" refers to TPA and derivatives therefrom recovered from a polymeric material. For example, according to one method, recovered TPA can be produced from scrap PET by extruding crushed PET in the presence of a depolymerization agent and/or acid catalyst. Another known method of producing recovered TPA involves steam-treating scrap PET to obtain PET particulates, which can then be combined with methanol to form an aerosol. The aerosol can be passed through a heated reaction zone in the presence of excess methanol vapor to recover the glycol and/or terephthalic acid monomers. Alternatively, recovered TPA can be obtained by passing superheated methanol vapor through a heated mixture comprising pieces of scrap PET and glycol and/or terephthalic acid oligomers. Depending on the recovery method selected, the recovered TPA can be in the form of a wet mixture, a dry mixture, or any combination thereof.

As illustrated in FIG. 1, the recovered TPA exiting TPA recovery facility 14 can subsequently be routed via transportation mechanism 116 to PET production facility 16. Transportation mechanism 116 can be any device operable to carry recovered TPA a distance of less than about 2 miles, less than about 1 mile, less than about 0.5 miles, or less than 0.25 miles to PET production facility 16. In one embodiment, transportation mechanism 116 can comprise a convey system.

PET production facility 16 can be a melt-phase polyester production facility capable of producing a variety of polyesters from a variety of starting materials. In general, PET production facility 16 can comprise two main stages. In the first stage starting materials, such as, for example TPA in conduits 114 and/or 116 and alcohol (e.g., ethylene glycol) in conduit 118 react to form monomers and/or oligomers. In the second stage, the monomers and/or oligomers react further for form the final polyester product. If the starting materials entering the first stage via conduits 114 and/or 116 include acid end groups, such as, for example, terephthalic acid or isophthalic acid, the first stage is referred to as esterification. If the starting materials in conduits 114 and/or 116 have methyl end groups, such as, for example, dimethyl terephthalate or dimethyl isophthalate, the first stage is referred to as ester exchange or trans-esterification. For simplicity, the term "esterification" as used herein, includes both esterification and ester exchange reactions. According to one embodiment of the present invention, esterification can take place at a temperature in the range of from about 180° C. to about 300° C., or about 235° C. to about 290° C., or 245° C. to 280° C. and a pressure of less than about 25 psig, or a pressure in the range of from about 1 psig to about 10 psig, or 2 psig to 5 psig. In one embodiment, the average chain length of the monomer and/or oligomer exiting the esterification stage can be less than about 25, from about 1 to about 20, or from 5 to 15.

The second stage in PET production facility 16 can be referred to as the polycondensation stage. The polycondensation stage can be a single step process, or can be divided into a prepolycondensation (or prepolymerization) step and one or more final (or finishing) polycondensation steps. Generally, longer chain polymers can be produced via a multi-stage polycondensation process. The polycondensation stage can be carried out at a temperature in the range of from about 220° C. to about 350° C., or about 240° C. to about 320° C. and a sub-atmospheric (e.g., vacuum) pressure. When polycondensation is carried out in a multi-stage process, the prepolymerization (or prepolymer) reactor can convert the monomer exiting the esterification stage into an oligomer having an average chain length in the range of from about 2 to about 40, from about 5 to about 35, or from 10 to 30. The finisher reactor then converts the oligomer/polymer mixture into a final polymer product having the desired chain length.

As illustrated in FIG. 1, one or more additives can be injected into any location within the esterification and/or polycondensation stages of PET production facility 16 via conduit 120. Suitable additives can include, for example, trifunctional or tetrafunctional comonomers, such as trimellitic anhydride, trimethylolpropane, pyromellitic dianhydride, pentaerythritol, or other polyacids or polyols; crosslinking or branching agents; colorant; toner; pigment; carbon black; glass fiber; filler; impact modifier; antioxidant; UV absorbent compound; and oxygen scavenging compound.

Generally, the produced TPA exiting TPA production facility 12 and/or the recovered TPA exiting TPA recovery facility 14 can be introduced into the esterification stage of PET production facility 16. In general, the TPA introduction method and/or mechanism can depend on several factors including the esterification reactor configuration employed and the physical state of the TPA entering PET facility 16. In one embodiment, the TPA can be introduced as a paste from a mechanically-agitated paste tank. In another embodiment, solid TPA can be introduced into the esterification stage of PET production facility 16 through a pressure reducer, such as, for example, an eductor. In one yet-to-be discussed embodiment wherein a recirculation fluid is employed, the TPA, which can be in the form of a liquid, solid, or any combination thereof, can be combined with a recirculation liquid prior to entering esterification reactor. In one embodiment, the combination of TPA with the recirculation liquid can be accomplished by direct addition through a pressure reducer and requires substantially no mechanical agitation (i.e., no paste tank).

The reactor configuration of the esterification and/or polycondensation stages of PET production facility 16 can vary. In one embodiment, the esterification stage of PET production facility 16 can employ a reactor that comprises a reactive distillation column. The reactive distillation column can contact liquid acid (i.e., terephthalic acid) with gaseous alcohol (i.e., ethylene glycol) in a countercurrent manner using distillation column internals, such as for example, trays, in order to facilitate the esterification reaction. In another embodiment of the present invention, PET production facility 16 can utilize one or more continuous stirred tank reactors (CSTRs) in the esterification stage. When multiple CSTRs are employed, the reactors can be operated in series or in parallel. CSTRs can employ baffles, agitators, and/or internal heating coils to facilitate heat and mass transfer in order to promote the esterification reaction of acid and alcohol into PET or other polyester.

In accordance with one embodiment of the present invention, less than about 50 percent, less than about 25 percent, less than about 10 percent, less than about 5 percent, or substantially none of the agitation of the liquid phase reaction medium processed in the esterification reactor of PET production facility 16 is provided by mechanical agitation. For example, in one embodiment, the esterification stage of PET production facility 16 can employ an axially elongated, substantially cylindrical pipe reactor. The pipe reactor can receive solid and/or fluid reactants proximate its inlet in order to produce monomer and/or oligomer from its outlet. The pipe reactor can be substantially horizontal, substantially vertical, or any variation thereof. In one embodiment, the esterification pipe reactor can include one or more heat exchange mechanisms (i.e., jacketed pipe) in order to provide additional heating and/or cooling to the reaction medium flowing therethrough. The pipe reactor can be substantially empty or can comprise one or more weirs to control reaction residence time. In another embodiment, the esterification stage of PET production facility 16 can comprise a reaction zone, a disengagement zone, and a distillation zone. The reaction zone can convert the solid and/or fluid reactants into an esterification medium comprising monomer and/or oligomer. The esterification medium from the reaction zone can be routed to the disengagement zone, which can facilitate the separation of gaseous by-products (i.e., water and alcohol) from the liquid esterification product (i.e., monomer and/or oligomer). The by-products can be separated in the distillation zone and the recovered alcohol can be reused within PET facility 16. In one embodiment, at least a portion of the liquid esterification product exiting the disengagement zone can be recycled back to the reaction zone as a recirculation fluid.

The monomer and/or oligomer exiting the esterification stage can subsequently be routed to a polycondensation stage (not shown) of PET production facility 16. As previously discussed, the polycondensation stage can comprise a single polycondensation step or can comprise two stages: the prepolycondensation step (i.e., the "pre-polymer stage") and the polycondensation step. The reactor configuration employed in the polycondensation stage of PET production facility 16 can vary. In general, melt phase polycondensation reactors can be designed to maintain a consistent average reaction residence time in order to control key product parameters such as, for example, final polyester chain length. In one embodiment, the polycondensation reactor configuration employed in PET production facility 16 can comprise one or more thin film or wipe film CSTRs. In another embodiment, the polycondensation reactor configuration can employ a reactive distillation column. In yet another embodiment of the present invention, the reactor configuration in the polycondensation stage can comprise a pipe reactor. Similarly to the pipe reactor previously described with respect to one embodiment of the esterification stage of PET production facility 16, a polycondensation pipe reactor can be substantially horizontal, substantially vertical, or any variation thereof and can additionally include a heat exchange mechanism (i.e., jacketed pipe) to provide additional heating and/or cooling to the reaction medium. In one embodiment, a pipe reactor employed in the polycondensation stage can be substantially empty or it can include one or more weirs for additional reaction residence time control. In one embodiment wherein a pipe reactor is employed in both the esterification and polycondensation stages of PET production facility 16, the esterification and/or polycondensation pipe reactors can be completely separate from each other or integrally combined in any way and to any degree.

Conventional melt-phase PET facilities cool and pelletize the molten polyester exiting the polycondensation stage in order to produce a transportable product. Typically, the cooled pellets are dried and devolatilized to remove acetaldehyde (AA) and other residual by-products before being shipped to customers and/or stored for future shipment. In contrast to the conventional processing schemes, in one embodiment of the present invention, at least a portion of the molten melt phase polyester exiting the polycondensation stage of PET production facility 16 can be routed directed to forming facility 20 via transportation mechanism 122. Transportation mechanism 122 can comprise a conveyor, a conduit and appropriate hydraulic and/or pneumatic driver, and/or any other suitable transportation means. According to one embodiment of the present invention, the temperature of the molten polyester (i.e., the PET "melt") transported to forming facility 20 via transportation mechanism 122 can be maintained above about 100° F., above about 200° F., or above 250° F.

Optionally, at least a portion of the melt phase polyester exiting the polycondensation stage of PET production facility 16 can be pelletized according to any method known in the art. Subsequently, at least a portion of the resulting pelletized PET can be sent to forming facility 20 via transportation mechanism 124 and/or shipped to customers and/or to storage via transportation mechanism 126. In one embodiment wherein pelletized PET is transported from PET production facility 16 to forming facility 20, integrated polyester production facility 10 can additionally comprise PET recycling facility 18. In PET recycling facility 18, previously used and/or scrap PET can be crushed into granules. The PET granules in transportation mechanism 128 can then be introduced into transportation mechanism 124, wherein the scrap PET granules can combine with the virgin PET pellets exiting PET production facility 16. In addition, at least a portion of the scrap PET granules exiting PET recycling facility 18 can optionally be routed via transportation mechanism 129 to PET production facility 16, as shown in FIG. 1. In order to ensure the polyester containing products formed from the combination of scrap and virgin PET maintain certain desired final properties, the weight ratio of scrap PET to virgin PET can be less than about 1:4, less than about 1:5, or less than about 1:8. As shown in FIG. 1, the stream comprising virgin and/or scrap PET particles can enter forming facility 20, wherein the stream can subsequently be heated to form molten PET to be molded into PET containers, as described in detail below.

As illustrated in FIG. 1, molten PET enters forming facility 20 via transportation mechanism 122. Forming facility 20 can be any facility capable of creating polyester-containing products from PET and other melt-phase polyesters. In one embodiment of the present invention, forming facility 20 can be capable of creating PET beverage containers, such as, for example PET bottles. In general, PET beverage containers can be formed by first molding molten PET into parisons or "preforms" via injection molding and then blow molding the hollow preforms into the desired size and shape. In general, forming facility 20 can employ a two-step molding process and/or a one-step molding process.

According to one embodiment of the present invention, forming facility 20 can employ a two-step molding process. The two-step forming process can occur in separate injection and blow molding facilities (not shown) that can be located at least about 5 miles, at least about 2 miles, at least about 1 mile, or at least about 0.5 miles apart. Molten PET entering forming facility 20 can first enter an injection molding facility (not shown) prior to being heated to a temperature in the range of from about 350 to about 650° F., about 400 to about 600° F., or 475 to 575° F. The warmed, molten polyester is then injected into a high pressure mold and rapidly cooled. The resulting preform, which is a beverage container precursor that resembles a thick test tube with a fully formed and threaded neck, is ejected from the mold and subsequently allowed to cool to a temperature of less than about 95° F., less than about 85° F., or less than 80° F. The cooled preform is then transported to a blow molding facility (not shown) or, optionally, shipped from integrated polyester facility 10 via transportation mechanism 130 for subsequent sale and/or storage. The preforms entering the blow molding facility can be heated to a temperature above the glass transition temperature of the PET or other polyester component or components. The warmed preform can then be simultaneously mechanically stretched in both the axial (via a core rod or mandrel) and radial (via a stream of compressed air) directions until the preform contacts the sides of the chilled mold, thereby forming the final desired shape. The simultaneous stretching in two orthogonal directions biaxially orients the PET molecules, which imparts additional strength and durability to the finished container.

According to another embodiment of the present invention, forming facility 20 can utilize a one-step molding process. In the one step molding process, the injection and blow molding facilities can be thoroughly integrated into a single molding apparatus having separate injection and blow molding cavities. This integration eliminates the cooling and reheating of the preform required by the above described two-step process. Typically, the temperature of the preforms can be maintained above about 100° F., above about 125° F., or above 150° F. during the transition between the injection and blow molding cavities. Similarly to the above-described process, molten polyester is injected into the injection molding cavity and rapidly cooled to generate a preform. The warm preform can be directly transferred to the blow molding cavity, wherein it is axially and radially stretched into the desired shape of the final container.

As illustrated in FIG. 1, empty PET beverage containers can exit forming facility 20 via transportation mechanism 132. Optionally, at least a portion of the empty containers can be transported less than about 5 miles, less than about 2 miles, less than about 1 mile, or less than about 0.5 miles via transportation mechanism 134 to filling facility 22, wherein the containers can be filled with a liquid beverage. Examples of suitable beverages can include, but are not limited to, carbonated soft drinks, water, juices, and alcoholic beverages such as beer. The method of filling the bottles depends in part on the physical properties of the bottles. For example, bottles having a higher temperature resistance can be produced for beverages, such as juices, that require hot filling techniques. Bottles containing soft drinks and other carbonated beverages can require additional strength and durability to withstand the carbonation-induced internal pressure, which can exceed over about 60 pounds per square inch (psi). In order to accommodate various requirements, in one embodiment, at least one adjustment can be made to the operating parameters of one or more upstream production facilities in order to produce containers suitable for various types of beverages. Once filled, the beverage containers can then be shipped out of integrated polyester production facility 10 via transportation mechanism 136 for subsequent storage and/or sale.

Although one embodiment of the integrated polyester processing facility was discussed above with respect to the production of polyethylene terephthalate and PET containing beverage containers, it should be understood that the present invention can be applied to the production of a wide variety of polyesters and polyester containing products in an integrated production facility. Examples of melt-phase polyesters that can be produced in accordance with the present invention include, but are not limited to, homopolymers and copolymers of polyethylene terephthalate (PET), PETG (PET modified with 1,4-cyclohexane-dimethanol (CHDM) comonomer), fully aromatic or liquid crystalline polyesters, biodegradable polyesters, such as those comprising butanediol, terephthalic acid and adipic acid residues, poly(cyclohexane-dimethylene terephthalate) homopolymer and copolymers, and homopolymers and copolymers of CHDM and cyclohexane dicarboxylic acid or dimethyl cyclohexanedicarboxylate.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

DEFINITIONS

As used herein, the terms "a," "an," "the," and "said" means one or more.

As used herein, the term "agitation," refers to work dissipated into a reaction medium causing fluid flow and/or mixing.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise," provided below.

As used herein, the terms "having," "has," and "have" have the same open-ended meaning as "comprising," "comprises," and "comprise," provided above As used herein, the terms "including," "includes," and "include" have the same open-ended meaning as "comprising," "comprises," and "comprise," provided above.

As used herein, the term, "mechanical agitation," refers to agitation of a reaction medium caused by physical movement of a rigid or flexible element(s) against or within the reaction medium.

As used herein, the term "reaction medium" refers to any medium subjected to chemical reaction.

As used herein, the term "terephthalyl moieties" refers to a terephthalyl group with any end group or end group combination attached.

Claims Not Limited to Disclosed Embodiments

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. In a process for making a PET container wherein: (a) terephthalic acid (TPA) is produced in a TPA facility; and (b) at least a portion of said TPA product is used to produce a polyethylene terephthalate (PET) product in a PET facility for manufacturing PET; and (c) at least a portion of said PET product is used to make containers in a container forming facility, wherein the distance between said TPA facility and said PET facility is less than about 2 miles, and the distance between said PET facility and said container forming facility is less than about 2 miles, and the temperature of said TPA product between production in said TPA facility and use in said PET facility is maintained above about 100° F.

2. The process of claim 1, further comprising recovering terephthalyl moieties from scrap and/or used PET in a recovery facility and using at least a portion of the recovered terephthalyl moieties in said PET facility to produced said PET product, wherein the distance between said recovery facility and said PET facility is less than about 2 miles.

3. The process of claim 1, further comprising filling at least a portion of said containers with a liquid in a filling facility, wherein the distance between said forming facility and said filling facility is less than about 2 miles.

4. The process of claim 1, wherein said TPA product is maintained in the form of a wet mixture between production in said TPA facility and use in said PET facility, wherein said wet mixture comprises at least about 50 weight percent solid TPA particles and at least about 1 weight percent liquid.

5. The process of claim 4, wherein said wet mixture is a wet cake.

6. The process of claim 1, wherein the temperature of said PET product between production in said PET facility and use in said forming facility is maintained above about 100° F.

7. The process of claim 1, wherein step (c) includes making preforms from said PET product and blow molding said preforms into said containers.

8. The process of claim 7, wherein the temperature of at least a portion of said preforms is maintained above 100° F. between said making thereof and said blow molding.

9. The process of claim 1, wherein said TPA facility has a design production rate within about 15 percent of the design feed rate of said PET facility.

10. The process of claim 1 wherein said terephthalic acid produced in said terephthalic acid (TPA) facility, is a wet mixture comprising at least about 50 weight percent of solid TPA particles and at least about 1 weight percent of a liquid; and transporting said wet mixture from said TPA facility to the polyethylene terephthalate (PET) facility via a convey system; and introducing said wet mixture into said PET facility, wherein said PET facility has a design production rate greater than about 4,500 pounds per hour.

11. The process of claim 10, wherein the temperature of said wet mixture during said transporting is maintained above about 100° F.

12. The process of claim 10, wherein at least a portion of said transporting is carried out using a conveyor.

13. The process of claim 10, wherein said wet mixture comprises at least about 75 weight percent of said solid TPA particles and at least about 2 weight percent of said liquid.

14. The process of claim 10, wherein said liquid comprises at least about 50 volume percent water.

15. The process of claim 10, wherein said introducing of the wet mixture includes combining said wet mixture with a recirculation liquid and thereafter feeding the combined stream to an esterification reactor.

16. The process of claim 15, wherein said combining is accomplished without substantial mechanical agitation.

17. The process of claim 15, wherein said combining is carried out using an eductor.

18. The process of claim 1, wherein the temperature of said PET product between said PET production facility and use in said forming facility is maintained above about 100° F.

19. The process of claim 7, wherein the temperature of at least a portion of said preforms is maintained above 100° F. between said making thereof and said blow molding.

20. The process of claim 7, further comprising filling at least a portion of said containers with a liquid in a filling facility, wherein the distance between said forming facility and said filling facility is less than about 2 miles.

\* \* \* \* \*